(12) United States Patent  (10) Patent No.: US 7,568,580 B2
Fenton  (45) Date of Patent: Aug. 4, 2009

(54) DISPENSERS FOR TISSUE DILATOR DEVICES

(75) Inventor: Gustav R. Fenton, Minneapolis, MN (US)

(73) Assignee: CNS, Inc., Eden Prarie, MN (US)

( * ) Notice: Subject to any disclaimer, the term of this patent is extended or adjusted under 35 U.S.C. 154(b) by 902 days.

(21) Appl. No.: 10/881,232

(22) Filed: Jun. 30, 2004

(65) Prior Publication Data

US 2005/0189372 A1 Sep. 1, 2005
US 2008/0302814 A9 Dec. 11, 2008

Related U.S. Application Data

(63) Continuation of application No. PCT/US02/41541, filed on Dec. 27, 2002.

(60) Provisional application No. 60/346,154, filed on Dec. 31, 2001.

(51) Int. Cl.
*A61F 15/00* (2006.01)
*B65H 5/28* (2006.01)

(52) U.S. Cl. .......................... 206/390; 206/441; 221/71

(58) Field of Classification Search ................. 206/390, 206/820, 440, 339, 441, 391; 221/231, 71, 221/25, 74; 606/199
See application file for complete search history.

(56) References Cited

U.S. PATENT DOCUMENTS

| | | | |
|---|---|---|---|
| 3,530,494 A | 9/1970 | Baratta | |
| 4,465,208 A | 8/1984 | Buban et al. | |
| 4,653,666 A | 3/1987 | Mertens | |
| 4,872,593 A | 10/1989 | Behringer | |
| 5,005,730 A * | 4/1991 | Pickrell et al. | 221/71 |
| 5,056,683 A | 10/1991 | O'Brien et al. | |
| 5,065,894 A * | 11/1991 | Garland | 221/25 |
| 5,133,477 A * | 7/1992 | Etheredge et al. | 221/25 |
| 5,271,522 A | 12/1993 | Ko et al. | |
| 5,353,956 A | 10/1994 | Wilson | |
| 5,358,140 A | 10/1994 | Pellegrino | |

(Continued)

FOREIGN PATENT DOCUMENTS

GB 2123386 A 2/1984
WO 99/22678 A1 5/1999

OTHER PUBLICATIONS

Supplementary European Search Report For European Patent Application No. 02796087.1; Date of Mailing: Jan. 4, 2008; 3 pages.
PCT/US02/41541 International Search Report, filed Jun. 17, 2003, CNS, Inc.

*Primary Examiner*—Mickey Yu
*Assistant Examiner*—Steven A. Reynolds
(74) *Attorney, Agent, or Firm*—Laura K. Madden; Theodore R. Furman

(57) ABSTRACT

Dilator dispensers and mounting apparatus and methods of dispensing and mounting nasal dilators to enable dilation to external tissue are provided. An apparatus may be used with a variety of types and sizes of dilator devices, including traditional elongate dilator devices for humans and animals such as horses, dogs and the like. A compact, portable, protective dilator dispenser is provided so that a user may readily access and apply a dilator device at any time. A combined apparatus including a dilator dispenser and a mounting aid is provided for a dilator device so that a dilator device may be quickly, easily and accurately applied by a user.

23 Claims, 14 Drawing Sheets

U.S. PATENT DOCUMENTS

| | | |
|---|---|---|
| 5,497,904 A | 3/1996 | Jones |
| 5,511,689 A | 4/1996 | Frank |
| 5,533,499 A | 7/1996 | Johnson |
| 5,649,642 A | 7/1997 | Mabry et al. |
| 5,782,786 A | 7/1998 | Tomaiuolo |
| 5,842,469 A | 12/1998 | Rapp et al. |
| 5,938,070 A * | 8/1999 | Welborn et al. ............... 221/73 |
| 5,939,161 A | 8/1999 | Callahan, Jr. |
| 6,050,449 A | 4/2000 | Kanj |
| 6,065,470 A | 5/2000 | Van Cromvoirt et al. |
| 6,098,616 A * | 8/2000 | Lundy et al. ............ 128/200.24 |
| 6,213,343 B1 * | 4/2001 | Damikolas .................... 221/25 |
| 6,240,989 B1 | 6/2001 | Masoud |
| 6,267,264 B1 | 7/2001 | Spina et al. |
| 6,318,362 B1 | 11/2001 | Johnson |
| 6,923,320 B2 * | 8/2005 | Grossman ................... 206/440 |

* cited by examiner

DISPENSERS FOR TISSUE DILATOR DEVICES

RELATED APPLICATIONS

This application is a continuation of International Application No. PCT/US02/41541, filed Dec. 27, 2002, which claims the benefit of priority of U.S. Provisional Application No. 60/346,154, filed Dec. 31, 2001.

FIELD OF THE INVENTION

The present invention relates to the field of tissue dilator devices. In particular, the present invention relates to a family of nasal dilator dispenser devices and aids to mounting nasal dilator devices for use in dilating tissue to improve respiration of a user.

BACKGROUND OF THE INVENTION

The field of endeavor related to dilation of nasal passages and adjacent tissue using over the nose-type dilator devices has a short and active history. One active participant and innovator in this field is the owner of this patent disclosure, CNS, Inc. of Eden Prairie, MN (CNS). Recently, CNS has introduced nasal dilators for human and equine use to dilate nasal passageways in an attempt to ease respiration and increase volumetric flow during respiration, among other things. These prior art dilator devices are typically packaged for single use only and no accompanying materials or devices are included in any packaging delivered in conjunction with the dilator devices. Representative U.S. patents disclosing prior art nasal dilators include U.S. Pat. No. 6,098,606; 6,318,362; 6,065,470; and 5,533,499, each patent being incorporated by reference herein.

Historically, nasal dilators have been packaged in individual packages that must be opened so the user can apply the dilator. These individual packages are oftentimes packaged as a set in a single package or box so the user must typically open the box, extract a single dilator package, open the dilator package and apply the dilator. This prior art packaging adds cost, is cumbersome and increases the difficulty of applying a dilator for the average user. Often, the dilator devices were merely placed inside a pasteboard box having adhesive bonds for structural integrity.

The prior art packaging of over the nose dilator devices inhibits a user from quickly obtaining a dilator device and thus likely decreases the frequency of use of dilator devices by the user. Furthermore, if a user wants to carry a single dilator device in most cases a single unit is not protected and will degrade from casual contact, even if unopened. Thus, an increased likelihood of damage to the dilator arises such that the dilator may be damaged and unusable. Then, if a user has a momentary desire to temporarily increase respiration through their nasal passages, such as when dining, drinking, exercising, sleeping, resting or the like, the prior art packaging mechanisms do not support such uses.

Prior art dispensing apparatus for elongate objects such as labels, chewing gum in stick form, adhesive bandages, business cards and the like have long been known and used in the art. For example, U.S. Pat. No. 5,497,904 issued to Jones on Mar. 12, 1996 disclose a improved gum label dispenser in which a portable waist mounted adapted to carry a roll of gum label. U.S. Pat. Nos. 5,353,956; 4,465,208; 5,056,683 and 5,649,642 each disclose improved chewing gum dispensers in which a single stick of chewing gum is manually ejected from a rectangular container. U.S. Pat. Nos. 4,653,666; 4,872,593; 5,271,522; 5,358,140; 5,782,786 and 5,939,161 each disclose an apparatus for dispensing adhesive bandages and the like. U.S. Pat. Nos. 6,050,449; 6,240,989; and 6,267,264 each disclose an apparatus adapted for dispensing business cards. Each of these prior art patents are incorporated by reference herein. None of these prior art approaches for dispensing single articles appears to solve issues unique to the storage and use of dilator devices.

Thus a need exists in the art for a compact, portable, protective dilator dispenser so that a user may readily access and apply a dilator device at any time. A need exists in the art for a dispenser that physically guards nasal dilator devices from damage prior to use. A need exists in the art for a combined dispenser and mounting aid so that a nasal dilator may be quickly, easily and accurately applied by a user.

SUMMARY OF THE INVENTION

The present invention teaches, enables, illustrates, describes and claims new, useful and non-obvious dilator dispensers and mounting apparatus and methods of dispensing and mounting said nasal dilators to provide dilation and thereby improve respiration for a user.

The present invention provides a dispenser for dilator devices having a package which contains a connected plurality of dilator devices. The package includes at least one aperture through which dilator devices pass prior to being separated and used.

The apparatus of the present invention may be used with a variety of types and sizes of dilator devices, including traditional elongate dilator devices for humans and animals such as horses, dogs and the like. The present invention may be configured for placement in a retail setting on a shelf, display rack, or hanging from a fixture having purely ornamental features added without departing from the teaching of the present invention (and which may independently form the basis of design patent rights, trademark rights, trade dress rights and copyrights).

The dilator apparatus of the present invention may be configured to be refilled by the user with additional dilator devices or the apparatus may be rendered as entirely disposable or recyclable without departing from the spirit and scope of the present invention. The apparatus of the present invention may be scaled in size to accommodate different size dilator devices and a different unit count of dilator devices disposed therein.

The dilator apparatus of the present invention may preferably include combinations of items useful in conjunction with application and use of a dilator device. For example, degreasing agents suspended in fluid and/or impregnated into a portion of cloth or sheeting or having a releasable soapy fluid or powdered soap material. Dilator alignment tools and mounting aids, dilator shaping and tempering structures (to create a desired shape of a dilator or segment of a dilator). Dilator lifting-force adjustment structure, dilator cutting (and/or related measuring) structures are also disclosed herein. In addition, primary or secondary adhesive materials for retaining a dilator device to tissue and use of a reflective surface so that a user can confirm dilator placement and alignment. Diverse dilator release liner removal structures, scented materials, therapeutic materials (e.g., aspirin, decongestant, salve, balm, cough drops, tea, etc.) and the like are also disclosed herein, each of which may accompany the dispenser(s) and/or the individual dilator devices disclosed herein in a nasal dilation kit. Examples of such nasal dilation kits include devices and fluids which promote use of the dilator for a given application. For example, a nasal dilator sleep kit might contain degreasing pads, a reusable eye shade (or cover) into which a dilator may be incorporated, a cold/sinus recovery kit might include degreasing pads, dilator devices, lip/nose balm, heat/cold packs and aspirin or the like, and a nasal dilator exercise kit might include sunscreen, reflective dilators, degreasing pads and a stopwatch or timer.

The primary embodiments of the present invention are intended to dispense, or meter, a single dilator device at a time. Related embodiments of the present invention include dispenser devices for dilator devices which are analogous to coin operated vending equipment. That is, a dispenser device which delivers one or more dilator devices in exchange for value received from a user of the dispenser. These dispenser devices may operate in response to a user depositing coins or paper currency, placing an essentially non-cancelable order via telephone, over a global computer network or with a a value card having electronically- or magnetically-read/write information, including information regarding the user, stored therein.

A further embodiment of the present invention includes dispenser devices which operate on a periodic basis (e.g., automatically dispense a dilator at a set time) or which dispense a dilator device in response to a signal from a user, such as a snore signal (received by a so-called snore indicator) or in response to a signal indicating that a user is having an apneic event. In this further embodiment, a source of illumination may be energized when the dispenser is activated.

Another embodiment of the present invention for use in hospitals and overnight commercial accommodations is preferably wired or linked to a billing system so that for each dilator device dispensed a charge accrues to be settled later by the user/occupant.

An object of the present invention includes providing a compact, portable, dilator dispenser designed so that a user may readily access, configure, align and apply a dilator device at any time and said dilators are stored securely in a controlled, clean environment.

An object of the present invention includes providing a dilator dispenser that physically guards nasal dilator devices from damage prior to use.

A further object of the present invention includes providing a combined apparatus comprising a dilator dispenser and a mounting aid for a dilator device so that said dilator may be quickly, easily and accurately applied by a user.

These and other objects of the present invention are addressed and achieved by use of the present invention which is enabled, taught, disclosed, described, illustrated and claimed herein.

DETAILED DESCRIPTION OF THE PREFERRED EMBODIMENTS

The present invention encompasses a large variety of dispensers for tissue dilator devices 10 which may be packaged as a set 20 of many individual dilator devices 10. The present invention will now be briefly described with reference to the accompanying drawings and subsequent to such detailed description, a written description of various additional embodiments will be set out so that the reader may appreciate a slightly different perspective on the present inventions.

Figure 1A:
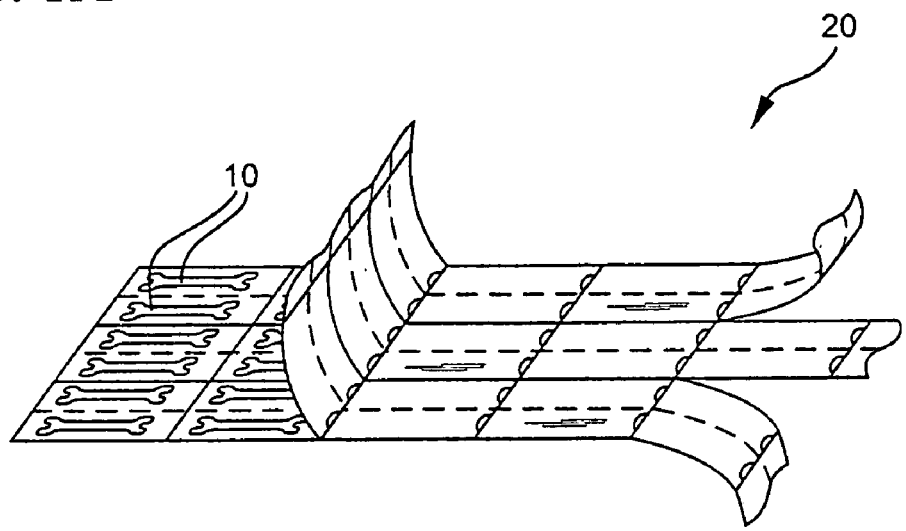
FIG. 1a and FIG. 1b are two prior art packaging for dilator devices in which each dilator unit is retained in a pocket formed between opposing sheets of material.
Figure 1B:
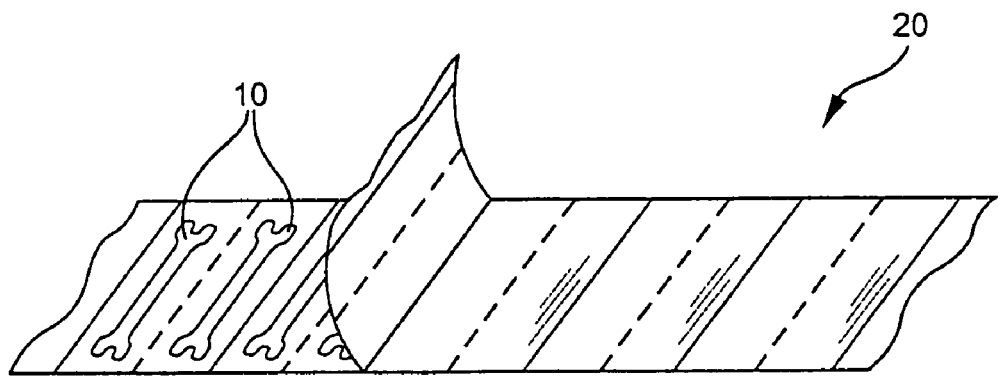

Referring now to FIG. 1a and FIG. 1b two prior art packaging structures 20 for individual dilator devices 10 are depicted in which each dilator unit 10 is retained in a pocket formed between opposing sheets of material. The material is typically sealed at the periphery around each dilator 10 with a cold set or other type adhesive material. The packaging structures 20 are then usually packed into a re-sealing paper or cardboard box (not shown) which is sealed using traditional techniques.

Figure 2A:
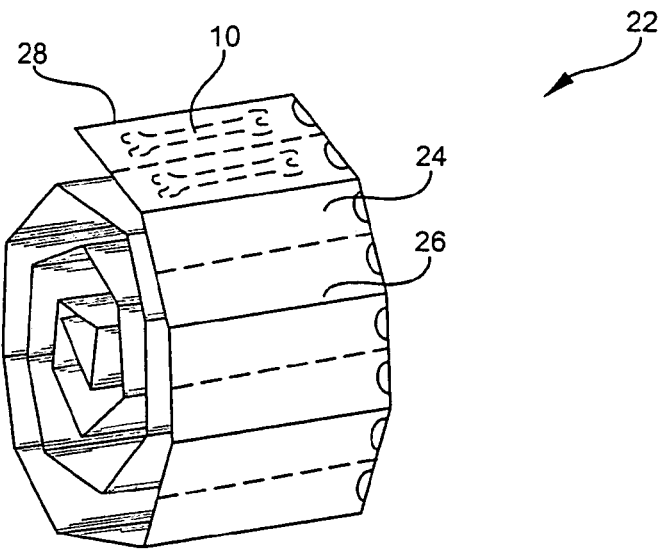
FIG. 2a and FIG. 2b depict an embodiment of the present invention wherein the dilator device packaging is formed into an elongate sheet having a plurality of pockets formed therebetween to receive a like plurality of dilator devices.
Figure 2B:
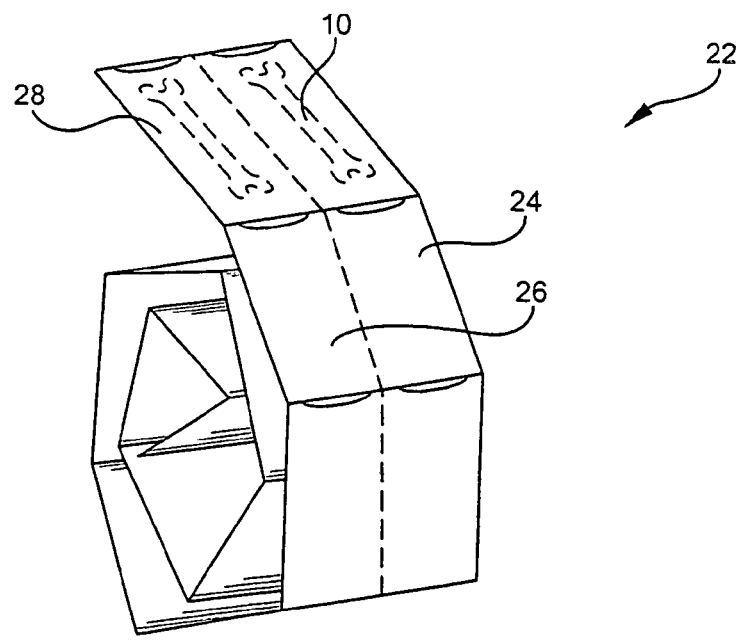

Referring now to FIG. 2a and FIG. 2b which depict an embodiment of the present invention wherein a new configuration of dilator device packaging 22 is formed into a roll shape composed of two elongate sheets of material 24,26 having a plurality of individual pockets 28 formed therebetween to receive a like plurality of individual dilator devices 10 shown in ghost in FIGS. 2a and 2b.

Figure 3A:
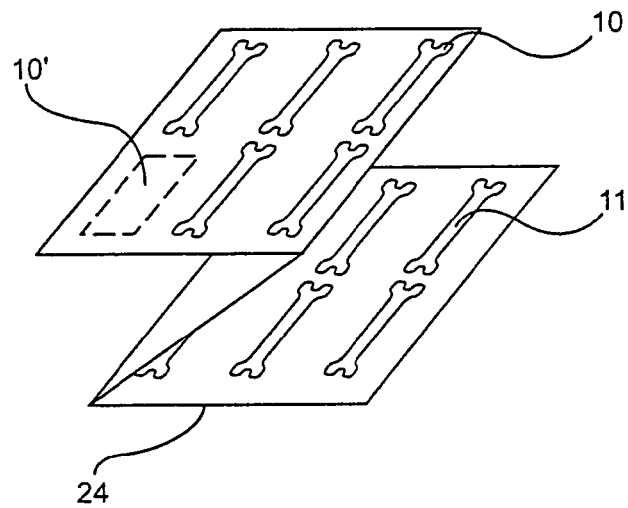
FIGS. 3a, 3b and 3c depicts several embodiments of a plurality of dilator devices each having a discrete placement location and wherein only a single sheet is used to retain the dilator devices in place prior to use.
Figure 3B:
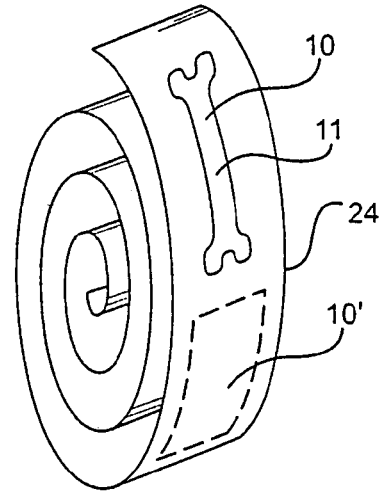
Figure 3C:
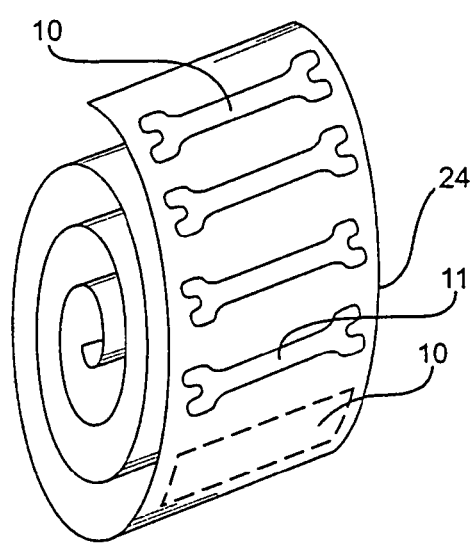

The three views depicted in FIGS. 3a, 3b and 3c illustrate several embodiments of the present invention wherein a plurality of dilator devices 10 each have a discrete placement location 10' (shown in ghost in all three views) and wherein only a single sheet of material 24 is used to retain the dilator devices 10 in place. Thus, an upper surface 11 of each dilator device 10, are essentially uncovered and unprotected vis-à-vis ambient conditions and with potential for being damaged by inadvertent contact unless disposed in a protective package or dispenser (not shown). FIG. 3 shows dilators 10 that are so-called "island placed" on the sheets 24 or rolls of liner material. These could be provided as they are shown or in a dispenser pack where they may be provided as refills.

Figure 4A:
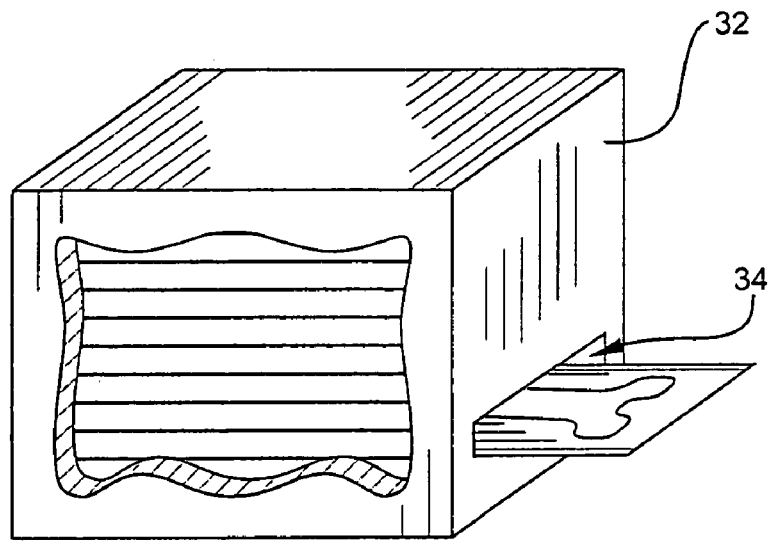
FIGS. 4a, 4b, 4c, 4d and 4e depict a family of related embodiments for a dilator dispenser apparatus, respectively including: a spring-biased package having a removal slot formed opposing the spring; a spring-biased "pop up" package having a sliding cover; a package for use with a "Z-fold" of sheets of material on which dilator devices are disposed; a package wherein a plurality of dilator devices are each suspended from a common frame member, and to access a dilator device a user merely tears one from the package; and a pull-out type package wherein when inverted, the dilator devices are readily manually accessible through an aperture formed in the package for the dilator devices.
Figure 4B:
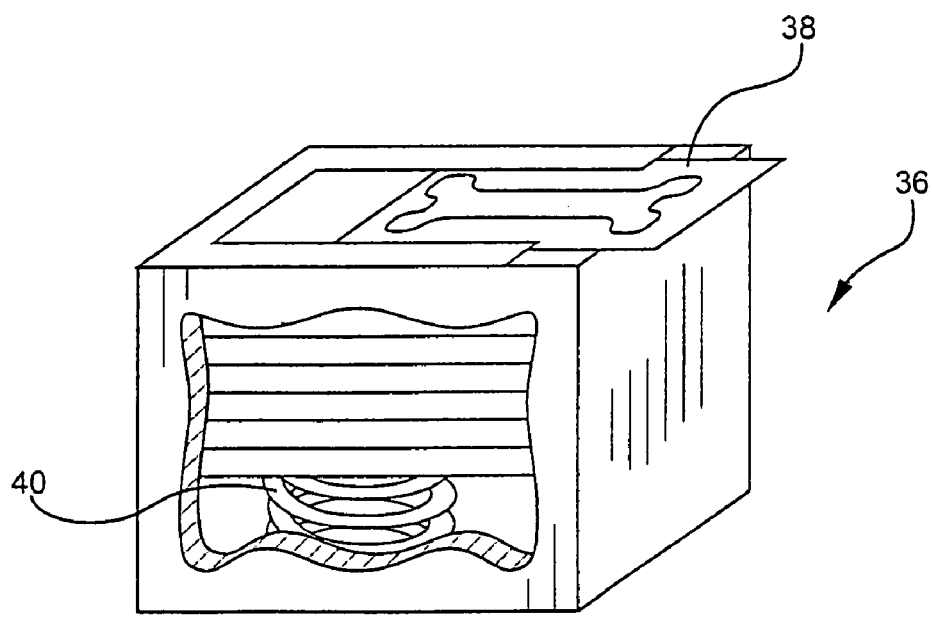

In each of FIGS. 4a, 4b, 4c, 4d and 4e a different one of a family of related embodiments for a dilator dispenser apparatus 30 are depicted. In FIG. 4a, a gravity feed (i.e., non-spring-biased) package 32 having a removal slot 34 formed at the lower portion of the package 32 (or which may oppose an upper gravity-assisting spring member—not shown). In FIG. 4b, a spring-biased "pop up" package 36 having a sliding cover 38 disposed opposite a spring member 40.

Figure 4C:
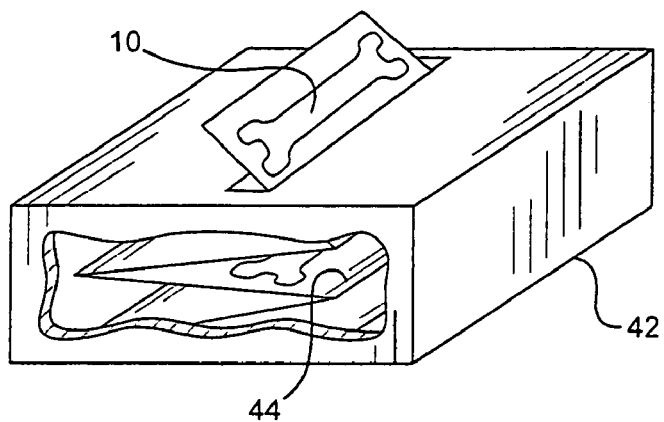
Figure 4D:
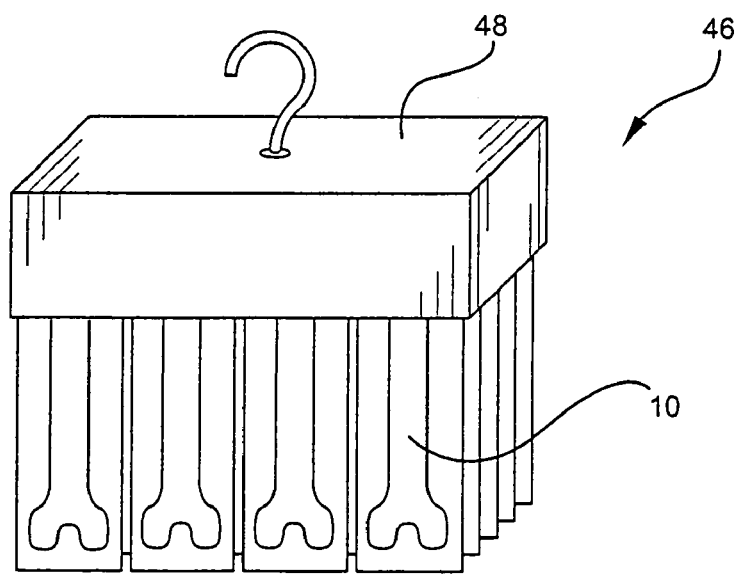
Figure 4E:
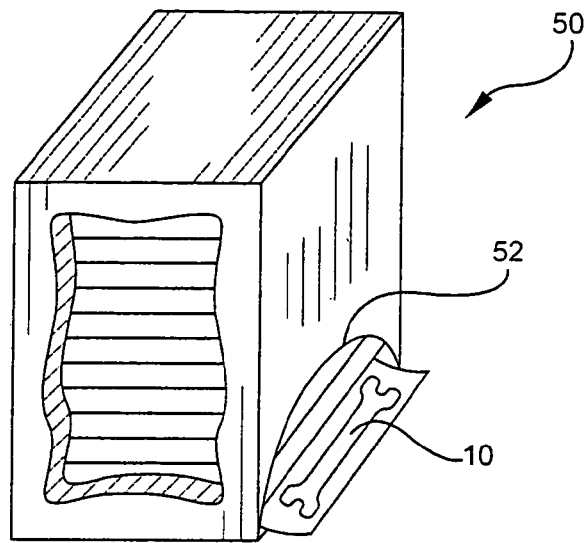

In FIG. 4c, a package 42 for use with a "Z-fold" of sheets of material 44 on which dilator devices 10 are disposed In FIG. 4d, a package 46 is illustrated wherein a plurality of dilator devices 10 are each suspended from a common frame member 48, and to access a dilator device 10 a user merely tears one from the package 46;

In FIG. 4e, a gravity-fed pull-out type package 50 is depicted wherein when the package 50 is inverted, the dilator devices 10 are readily manually accessible through an aperture 52 formed in the package 50 for use in manually retrieving the dilator devices 10.

In each embodiment depicted in FIGS. 4a through 4e, a typically elongate dilator device 10 may be oriented so that the dilator device is retrieved parallel to, or perpendicular to, the slot, aperture or opening of the respective package member. In addition, in the spring-biased embodiments of the present depicted, the spring may be a helical spring, a leaf spring, a material having a spring constant such as a foam or elastic material and the like. Such a spring member may be formed of metal, resin, foam, rubber or may be of any material which provides a biasing force when compressed. Other means of producing an equivalent biasing force may also be used in conjunction with, or in lieu of, the spring members illustrated or described. That is, structure that produced tension such as a rubber band or elastic segment of material may be employed to bias the dilator devices 10 toward an opening in the dispenser packages 30. FIG. 4 shows several ideas for dispenser packs with FIG. 4d being very unique. FIGS. 4a, 4b, 4d and 4e are meant for singlet cold seals. FIG. 4c could be implemented with adhesive (rather than perforations at the creases) to create the z-fold shape.

Figure 5:
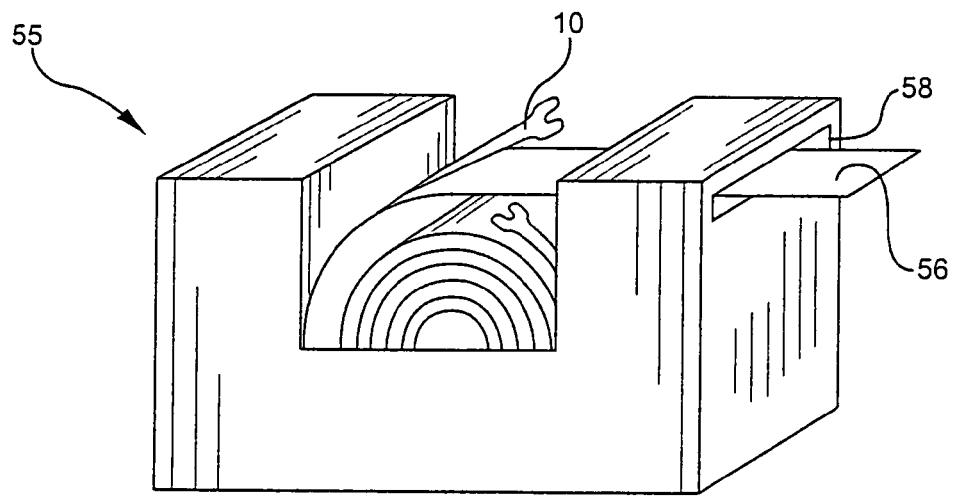
FIG. 5 is a perspective view depicting a roll of sheeting having a series of dilator devices disposed on one side which in operation are separated from the sheeting when the sheeting passes through a slot and the dilator device is manually accessible to a user.

Referring now to FIG. 5a, a dispenser device 55 similar to an adhesive tape dispenser is illustrated in a roll of sheeting 56 having a series of dilator devices 10 disposed on one side which in operation are separated from the sheeting when the sheeting passes through a slot 58 and the dilator device 10 is manually accessible to a user. The design of FIG. 5 uses a roll (similar to FIG. 3b) to allow the user to pop a dilator 10 as needed. The dispenser 55 could be decorative with refills of dilators capable of replacing used rolls. A related embodiment not depicted in FIG. 5 has at least one continuous resilient strip adhered to the sheeting 56 so that the resilient strip and sheeting 56 comprise a continuous dilator device. In use, a desired length of material is dispensed, severed, and applied to dilate nasal tissue just the same is now common when dispensing a length of adhesive tape.

Figure 6A:
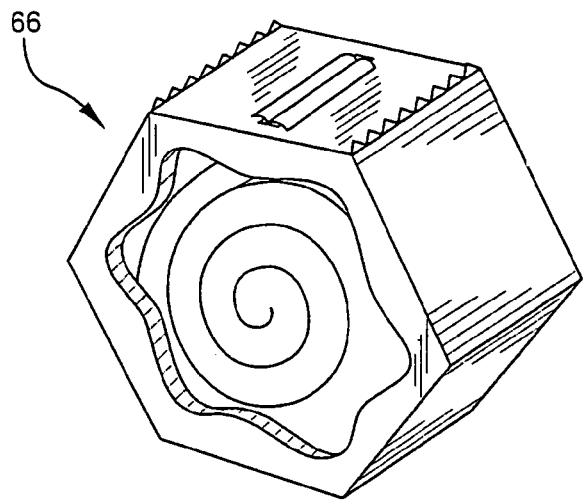
FIGS. 6a, 6b 6c and 6d depict a roll comprised of two sheets of material preferably cold-sealed to create a pocket for each dilator device disposed in a specially adapted dispenser, said roll of material, and a view showing how the cold-sealed sheets separate from the dilator device as the dilator emerges from the dispenser, respectively.
Figure 6B:
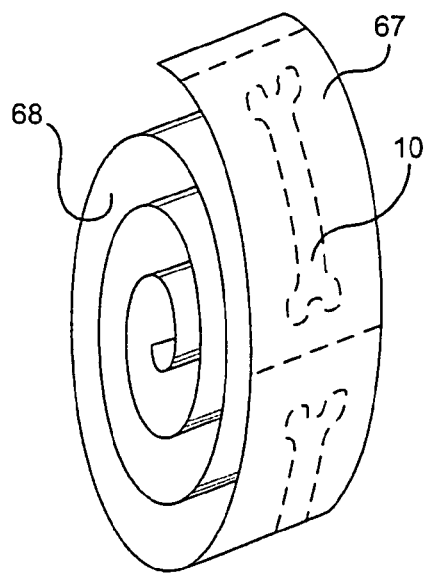
Figure 6C:
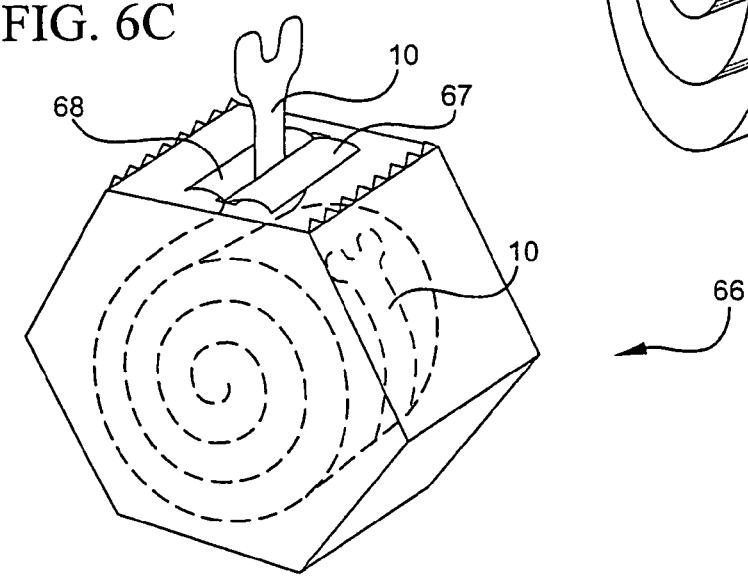

FIGS. 6a, 6b and 6c depict a roll-type dispenser 66 comprised of two sheets of material 67,68 preferably cold-sealed to create a pocket for each dilator device disposed in a specially adapted dispenser, said roll of material, and a view showing how the cold-sealed sheets separate from the dilator device as the dilator emerges from the dispenser, respectively. In FIG. 6 a continuous roll of cold sealed singlets that essentially pop a dilator up out of the center as the two sides of the cold seal are pulled. The serrated edges would be used to get rid of the accumulating cold seal material. The dispenser could be decorative with refills of dilators sold to fit.

Figure 6D:
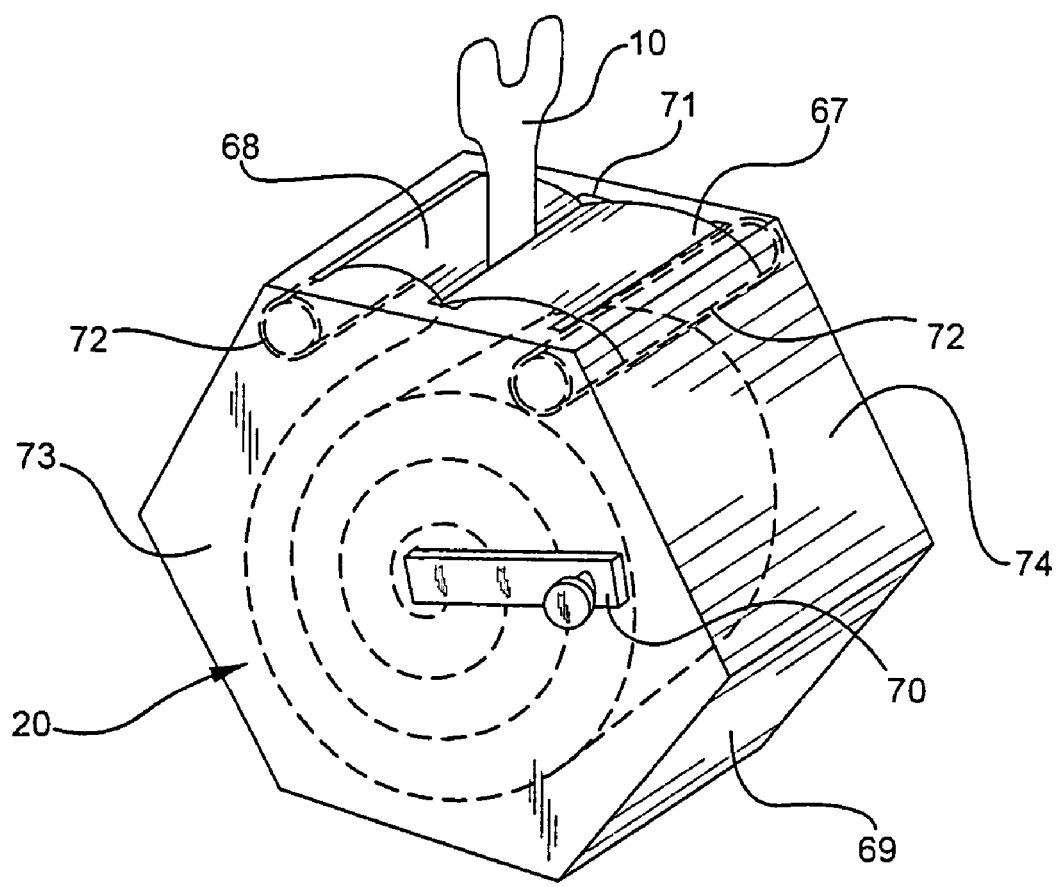
Figure 7A:
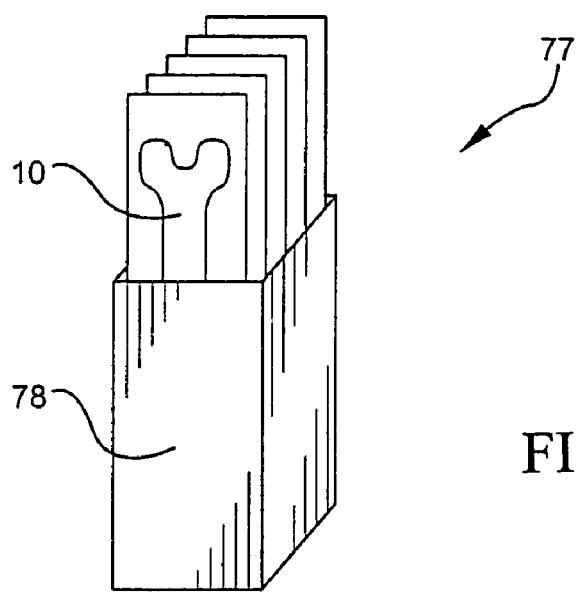
FIGS. 7a, 7b, 7c, 7d, 7e, and 7f are perspective views illustrating: a protective dispenser package (shown without a cover in FIG. 7a) for retaining and protecting a plurality of dilator devices; a dispenser wherein a plurality of dilators are retained by a common post or pin so that they remain together until used; a cup member sized to retain a plurality of dilator devices; an elongate container having a slot formed on one end from which dilator devices are manually extracted or ejected (by shaking the container); a soft package having an open end which may be tied off or sealed to retain the dilator devices therein; a hinged-lid (or clamshell style) package for dilator devices; and a friction fit hinged lid container which essentially locks when closed.
Figure 7B:
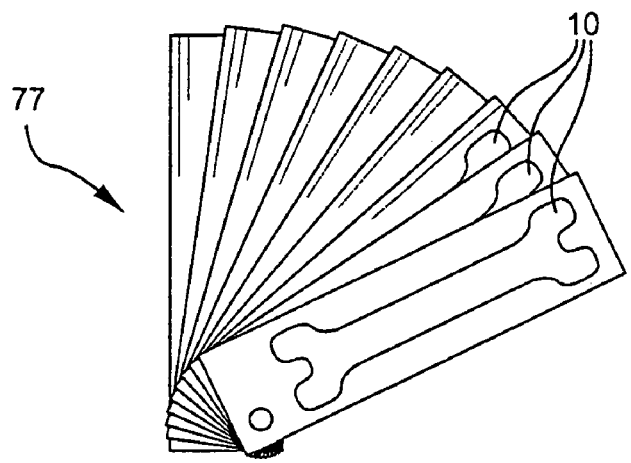
Figure 7C:
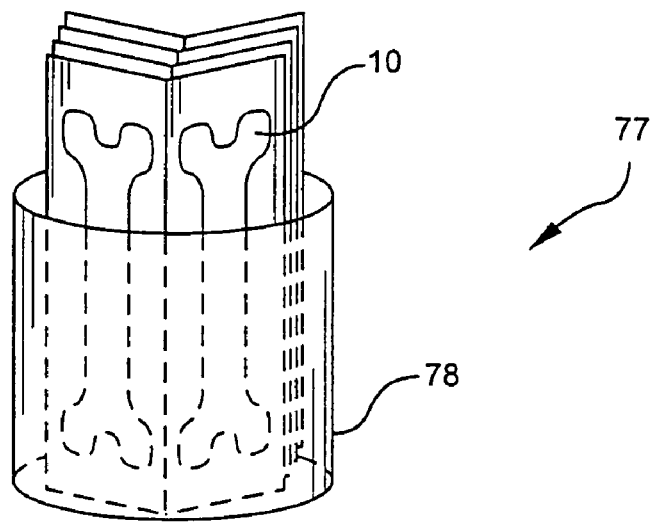
Figure 7D:
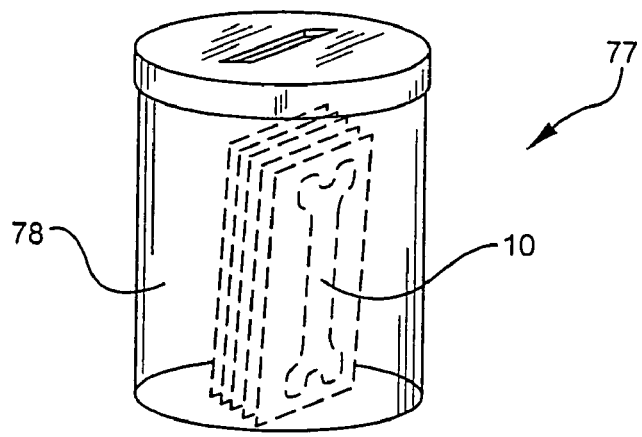
Figure 7E:
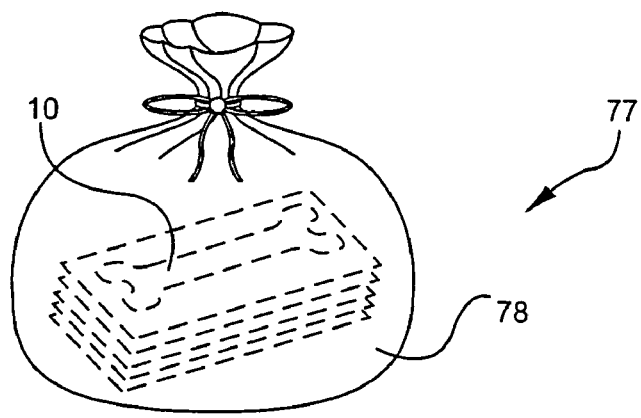
Figure 7F:
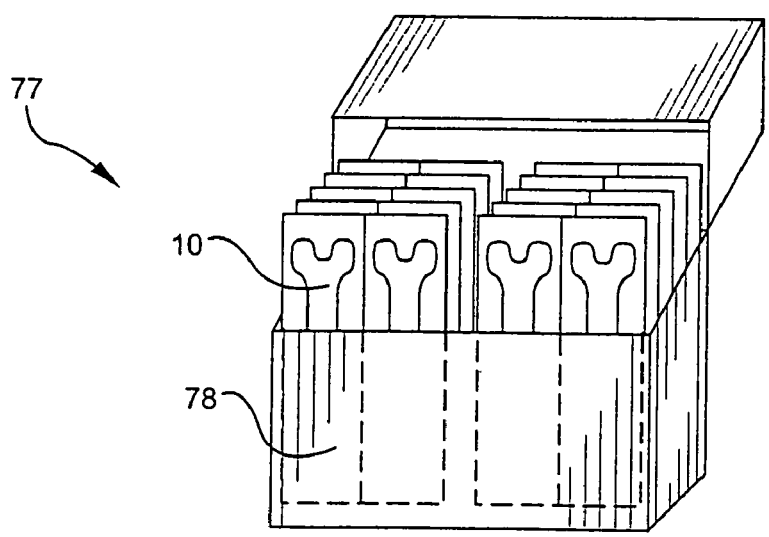

FIG. 6d illustrates another embodiment of a roll-type dispenser 69. A rolled set 20 of dilator devices 10 is held within dispenser 69. Rolled set 20 is rotatably held within dispenser 69. Rotation of set 20 may be in response to a user manipulation of component 70. Rotation of set 20 results in the dispensing of dilator devices 10 through aperture 71. Component 70 is illustrated to be a handle. Component 70 may alternatively be another user manipulable device such as a knob, disk, finger wheel, etc. After releasing dilator device 10, cold-sealed sheets 73 are captured within dispenser 69 upon take up rolls 72. Take up rolls 72 may be held in place between walls 73, 74 of dispenser 69. Take up rolls 72 may be mechanically coupled to handle 70 so that as dilator devices are extended out of dispenser, take up rolls are rotated to accept cold sealed sheets 67, 68. In one embodiment, take up rolls 72 may be coupled via gears to rotate in response to handle 70 being rotated.

FIGS. 7a, 7b, 7c, 7d, 7e, and 7f are perspective views illustrating a suite of dispenser types 77: a protective dispenser package or housing 78 (shown without a cover in FIG. 7a) for retaining and protecting a plurality of dilator devices; a dispenser wherein a plurality of dilators are retained by a common post or pin so that they remain together until used; a cup member sized to retain a plurality of dilator devices; an elongate container having a slot formed on one end from which dilator devices are manually extracted or ejected (by shaking the container); a soft package having an open end which may be tied off or sealed to retain the dilator devices therein; a hinged-lid (or clamshell style) package for dilator devices; and a friction fit hinged lid container which essentially locks when closed. FIG. 7 shows a variety of packages mostly for cold sealed singlets and doublets. Package 78 of dispenser 77 may be made of plastic, paper, fabric, or other known packaging materials.

Figure 8A:
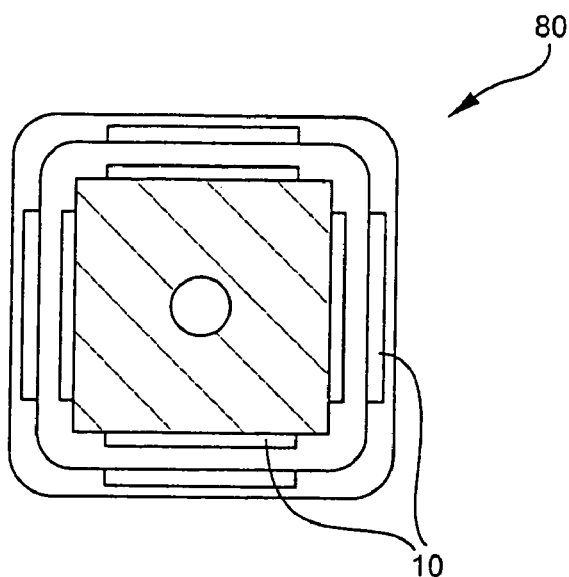
FIG. 8a and FIG. 8b depict two embodiments of a rotary dilator dispenser having a polygon shape so that each dilator device is disposed on an essentially flat portion of the polygon shape.
Figure 8B:
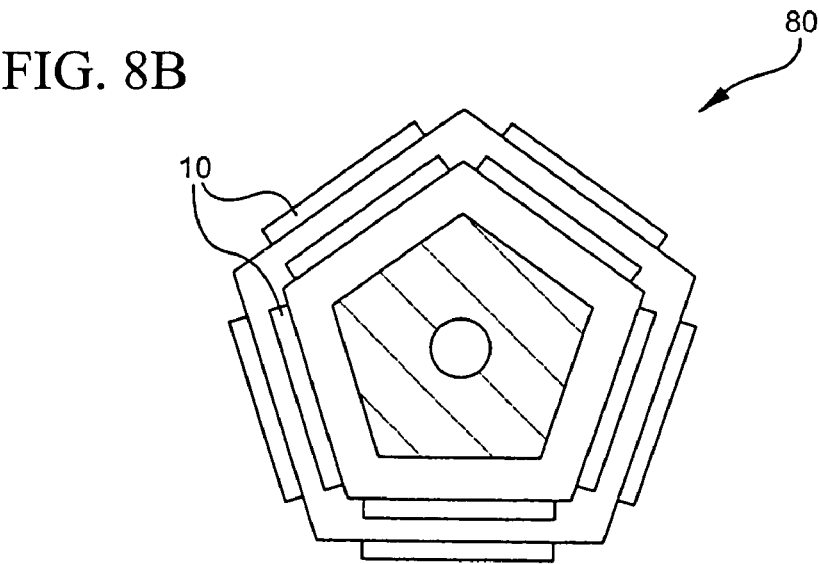

FIG. 8a and FIG. 8b depict two embodiments of a rotary dilator dispenser 80 having a polygon shape so that each dilator device 10 is disposed on a different portion of the polygon shape. These dispenser devices 80 may be adapted to couple to a band or belt which in turn couples around the wrist, waist or other extremity of a user. The dispensers 80 may be enclosed with a dispensing port for retrieving a dilator therefrom. The dispenser devices 80 are preferably rotatably coupled at an axis of rotation. If more than about two or three individual dilators 10 are disposed upon a flat surface portion, the spacing between successive dilator devices 10 should be increased so that each is not bent over a corner portion of the polygon shape.

Figure 9:
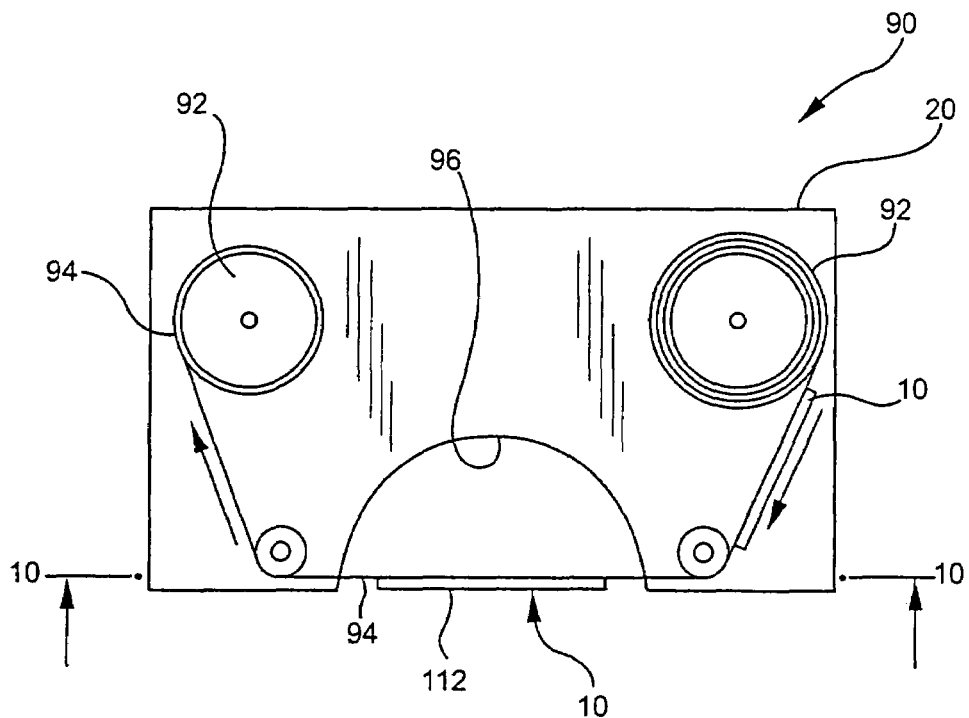
FIG. 9 is a plan view of a cassette-type dilator dispenser which has two rotary spools, a first having dilators coupled thereto and the other providing take-up of a transporter belt member so that a single dilator is suspended across an cutout portion of the dispenser for direct contact with the nose of user inserted therein.

FIG. 9 is a plan view of a cassette-type dilator dispenser 90 which has two rotary spools 92, 94, a first spool 92 having dilators 10 coupled to a transport belt or tape 94 and the other spool 92 providing take-up of the transport belt or tape 94 so that a single dilator 10 is suspended across a cutout portion 96 of the dispenser 90 for direct contact with the nose of user inserted therein.

Figure 10:
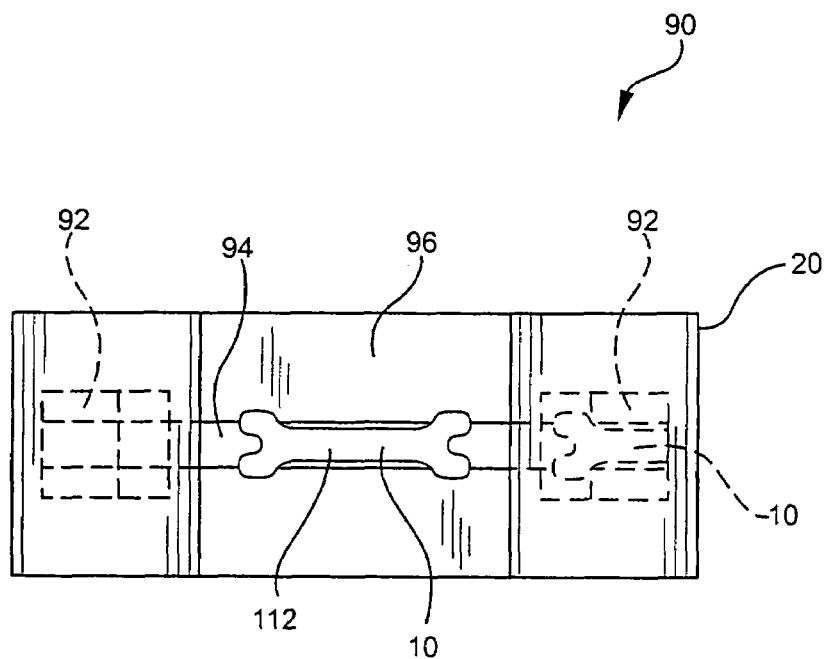
FIG. 10 is an elevational view taken along the lines 10-10 of FIG. 9 showing the single dilator suspended across the cutout portion.

FIG. 10 is an elevational view taken along the lines 10-10 of FIG. 9 showing the single dilator 10 suspended across the cutout portion 90.

Figure 11:
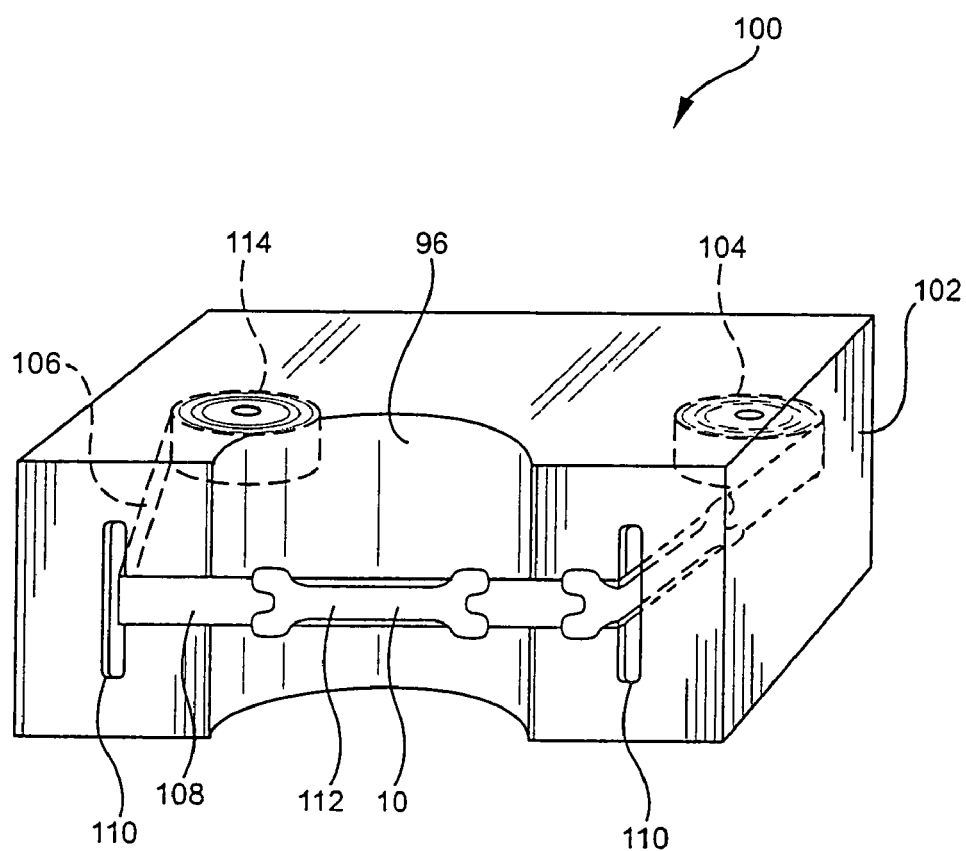
FIG. 11 is a perspective view of another dilator dispenser.

FIG. 11 is a perspective view of another dilator dispenser 100. Dispenser 100 may be sized to be graspable by an intended user. Different dispensers 100 may be differently sized, for example a child-sized dispenser 100 would be smaller than a dispenser 100 intended for adult usage. Dispenser 100 includes a graspable package 102 containing a connected plurality of dilator devices 10 and at least one aperture 110 or other passage through which the dilator devices 10 pass through prior to usage. The term "package" as used herein is broadly defined to include any container suitable for receiving dilator devices 10. For example, package 102 may be a single-walled or multiple-walled paper box. Package 102 may be an open container, similar to known clear tape dispensers, or may be a substantially closed box-like container. Package 102 may be of a plastic, paper, alternative materials, or combinations thereof. Package 102 may be a paper or plastic box for containing dilator devices 10. In this embodiment, package 102 contains a pair of spools 104, 106 each for receiving portions of a flexible tape 108. Flexible tape 108, which may be a plastic material, passes through a pair of apertures 110 of dispenser 100. Provided upon a surface of tape 108 are dilator devices 10. Dilator devices 10 may be adhesively secured to tape 108. A plurality of dilator devices 10 is initially held within spool 104. Dilator device 10 may include a release sheet 112 for exposing adhesive of the dilator device prior to use. Spools 106 may include a device 114 for rotating spool 106. Device 114 in this embodiment is a finger wheel which a user may manipulate to expose another dilator device 10. Finger wheel 114 extends through an aperture 115 of a sidewall of package 102 so that at least a portion of finger wheel 114 may be engaged by a user to advance dilator devices 10 into the cutout portion 96. Device 114 may take other forms, including but not limited to a knob or a disk. In another embodiment, spool 106 may be spring loaded to advance dilator devices from spool 104. Cutout portion 96 may include a different configuration to achieve the function of dispenser 100 as described herein with reference to FIG. 12. Padding (not shown) may be provided within cutout portion 96 to cushion the contact of dispenser 110 against the nose of a user when applying a dilator device 10.

Figure 12:
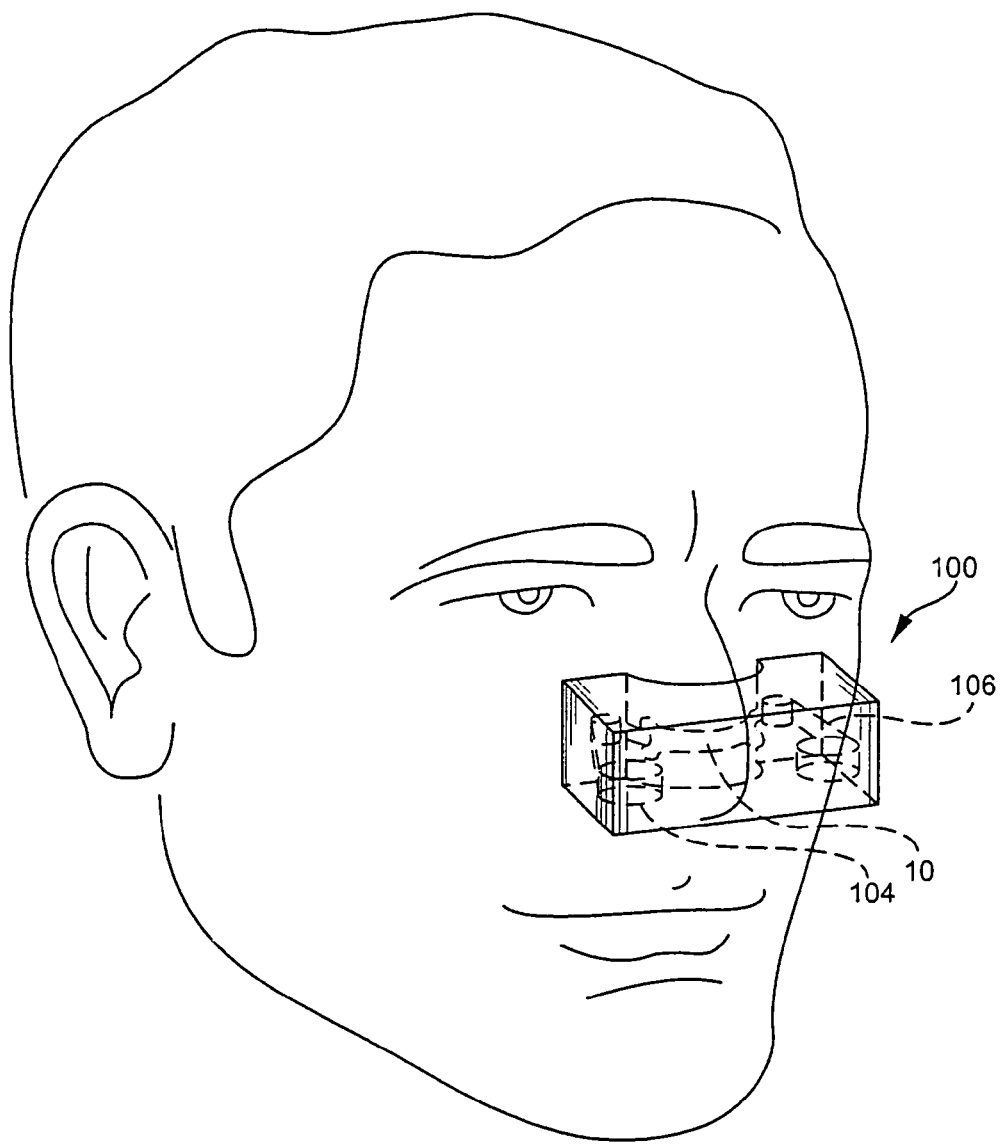
FIG. 12 is a perspective view of a dilator dispenser in use.

FIG. 12. illustrates a dispenser 100 in relation to a user. Steps of applying a dilator device 10 may include the steps of: advancing a dilator device 10 into the cutout portion 90 of dispenser 100; removing a release sheet 112 from dilator device 10; grasping dispenser 100 and directing cutout portion 90 toward nasal surfaces so that the dilator device 10 contact the nasal surface and is adhesively adhered thereto, and removing dispenser 100 away from nasal surfaces to release dilator device 10 in place. Such a method of applying dilator devices 10 to nasal surfaces may be particularly useful for children or adults with limited coordination or mobility.

The present invention shall now be described with only passing reference to the accompanying drawings so that the reader of this disclosure may gain added perspective into the operation of the various embodiments thereof.

The dispenser devices of the present invention may be scaled to provide a large number of dilator devices and may be configured to provide a selection among several different types of dilator devices. The inventors suggest that approximately 38 to 44 units of dilator devices are the minimum quantity to be provided by a so-called club sore dispenser pack; however no maximum number of units are to be implied or inferred from the teaching of this disclosure. The dispenser devices may package hang or adhere to a vertical surface or may be disposed on a horizontal surface, of course, most every embodiment of dispenser of the present invention may be a reusable dispenser which may be refilled. Preferred construction materials are cardboard or paperboard but any other material may be used, including metal, alloys of metal, resin or plastic material, composite material, glass, wood, and the like. The dispensers may be used with dilator packaging providing a dilator device on opposing sides of a sheet of liner material, dilator devices one side of a liner, one or more dilator device disposed in a pocket formed between two sheets of liner material. In the embodiments susceptible to use with roll-form extruded dilator devices, just the extruded dilator material and no liner material may be dispensed from a dispenser device. Note that roll-form dilator devices (such as depicted in FIG. 2b) may impart a shape memory to the dilator devices (particularly the devices disposed nearest the core of the roll). Such a shape memory may change the intended spring force for such dilator devices to the detriment of the user. On the other hand, the geometry of this type of dispenser may be used to increase or at least maintain the intended spring force of the dilator devices. On the contrary, the embodiment depicted at FIG. 2a will have less of a tendency to modify the intended spring force of the dilator devices dispensed therefrom.

Rotary Dilator Dispenser.

Another embodiment of the present invention comprises a rotary nasal dilator dispenser wherein a plurality of dilator devices are wound about a rotating portion and unwound by a user one at a time.

In a first form of this embodiment, the rotary nasal dilator dispenser has a rotating portion around which is wound a plurality of nasal dilator devices each connected to another dilator device and wherein the rotating portion is shaped, in cross section as a polygon preferably sized so that each dilator device lies on a substantially flat surface portion of said polygon. For example, if an octagon shaped rotating portion is adapted according to this form of this embodiment, preferably at least eight dilator devices would be disposed on each of the eight faces of the octagon. This embodiment may be used to house and dispense a large number of dilator devices wound about a variety of different shape rotating portions, and in this case, preferably the packaging for the dilator devices accommodates the increased spacing between said dilator devices for each successive layer of dilator devices.

In a second form of this particular embodiment, the rotary portion may be cylindrically shaped, may have a series of substantially flat portions (i.e., polygon), or may have a slight rise, or "crown," in lieu of such substantially flat portions and the dilator devices may be individually packaged or may be simply adhered to, or incorporated into, a length of adhesive-backed tape. In fact, a continuous length of resilient material (formed as one or more thin resilient strips) may be adhered to, or incorporated into, said length of adhesive-backed tape material and simply unwound by a user to a desired length, cut or severed from the remaining length of adhesive-backed material. Of course, the resilient material may be disposed on either or both sides of the adhesive tape material and if the roll has a single adhesive-backed side, the adhesive backed side may be on the lower portion or the upper portion of the roll (as same emerges from said dispenser). One advantage of having the adhesive-backed side on the upper portion stems from the fact that any crown or ridge shape assumed by any individual dilator device may be advantageously used to increase the magnitude of lifting force provided by the dilator device (i.e., any "shape memory" of the dilator device which causes same to assume an arcuate shape, may be employed by inverting the convex side of the dilator so that the crown or ridge abuts the nose of a user and then adhering same to the tissue to be dilated).

Tape-Type Dispenser.

A rudimentary form of this embodiment of the present invention comprises a dispenser similar in every respect to a dispenser for rolls of cellophane tape (either disposable or reusable) having a rotating portion constrained at the axis of rotation to a base member and having a sharp or serrated cutting instrument integrated into the dispenser spaced from the roll of cellophane tape. However, in lieu of a roll of cellophane tape, a roll of specially prepared continuous dilator material is disposed on the rotating portion that has adhesive on one side and at least one thin resilient structure coupled thereto that may be readily cut or severed by a user using the cutting instrument of said dispenser. The rotating portion may be integrated into the roll of specially prepared continuous dilator material or may itself be reusable as is known in the art of cellophane dispensers. In use, the user simply pulls a desired length of dilator material from the dispenser and manually severs the segment. If desired, the user applies the segment of dilator material to tissue to be dilated or the user may combine one or more such segments, one on top of another, to increase the effective lifting force provided by the segments. In this embodiment, the user may utilize cellophane tape or a similar, known and extant tape material (e.g., masking tape, medical tape, adhesive gauze, so-called first aid tape and the like).

Multi-Roll Tape-Type Dispenser.

Alternatively, two separate rolls of material may be disposed in a single dispenser along a common dispensing axis, or travel path, so that when a user extracts a segment of material the two materials are combined or adhered together to form a dual substrate article. A first roll preferably comprises a thin adhesive substrate having a width dimension and a second roll preferably comprises a resilient material having a smaller width dimension than the first roll. The resilient material may have adhesive material disposed on one or both sides thereof to promote lasting contact between the adhesive substrate and the resilient material. Optionally, incorporated into, or closely spaced from, the cutting instrument of the dilator dispenser a nip roller-type assembly, a single roller, or a smooth ridge feature may be implemented to establish firm contact between the thin adhesive substrate and the resilient material.

In this embodiment, the user may initially configure, and may freely to reconfigure, the dispenser apparatus to dispense dilator devices having diverse lifting forces simply by changing the roll of resilient material from a lower resiliency material to a higher resiliency material. Of course, the resilient material replaced by the user may be stored for later use. When just two rolls of material are used, the dispenser may be rendered more compact by configuring same so that each roll rotates in the opposite direction relative to the other roll. If more than two rolls of material is used (e.g., an upper and lower roll of thin adhesive material and an intermediate resilient material), they may all rotate in the same direction or some may be inverted and unwind in a direction opposite other of said rolls. Likewise, the dilator dispenser of the present invention may utilize dual sided adhesive tape material and/or adhesive disposed on the resilient material (or the resilient member itself may have an adhesive quality). Also, the rolls of material need not be spaced from each other, but may rest against other of said rolls to thus promote even dispensing of the diverse materials without undesirable slack, bubbles, kinks, or loops and the like. Any of the rolls of material may be spring-biased to engage other of said rolls of material and/or the rolls of material may be spring-biased so that they cannot freely unwind, but rather only unwind when sufficient force is applied to extract the material from the dispenser. In this form of the invention, a rachet-type mechanism is preferably used to ensure that the material does not retract into the dispenser after a segment of material is severed from its respective roll. If a rachet-type mechanism is used, the number of "clicks" of such mechanism may be used to indicate how much of the material has been dispensed and a user may be instructed (or may learn through trial and error) how many clicks corresponds to the appropriate size dilator device for that particular user.

For limited production runs manufacturing dilator devices, a large scale version of the above dispenser may be utilized. In lieu of adhesive bonding of the layers of the dilator devices thus produced, heat sealed or cold-stamped materials may be used. By simply adding a cutting utensil, the dilator devices may be cut into unit segments that may be individually packaged for use.

In all these embodiments of a roll-type dispenser for dilator devices leader tape or similar segment of non-dilator material may be added to minimize waste of the dilator device materials. Furthermore, while these roll-type dilator dispenser devices have been described in reference to common cellophane tape dispensers, no such limitation is intended and all said embodiments are susceptible of being incorporated into other forms. For example, a dispenser fabricated and used according to the foregoing may comprise a closed package with a single dilator dispensing slot or aperture. The package may have individual compartments for retaining each roll of material which are manually accessible for removal and replacement of said rolls of material. The compartments can be accessed via hinged or sliding flaps so that only the assembled dilator device is visible to the user during use of the dispenser.

In the above-described embodiments, the adhesive substrate and resilient member have been described as thin or flat portions of material, but they may comprise rope-like shapes or just the resilient material may be comprise such a rope-like shape (or may be geometrically shaped). If such materials are used, the dispenser will preferably accommodate the nearly inevitable "tracking" of such material as it is unrolled (i.e., like a garden hose wound around a cylinder). One manner of accommodating such tracking motion of the resilient material is to provide one or more guides (e.g., post, groove, peg, roller and the like) so that the material uniformly unwinds from the roll along a common axis, or travel path. If such rope-like or geometrically-shaped resilient material is used, the adhesive material may nonetheless comprise the thin adhesive substrate described above which is preferably a dual-sided adhesive substrate so that the resilient material is adequately coupled to the substrate and the substrate is adequately coupled to the nose of the user. Of course, if a dual-sided adhesive substrate is used, each side may have a different strength adhesive applied thereto as dictated by the intended usage and by the type and compatibility of the surfaces to be adhered.

Dilator Alignment Structures.

In another embodiment of the present invention, a dilator alignment structure is incorporated into either the exterior packaging or the dispenser for dilator devices. This dilator alignment structure preferably has a small amount of adhesive and/or at least two dilator retaining members to temporarily hold and retain a single dilator device at a time while the user aligns the dilator into position over the tissue to be dilated. In this form of the invention, the dilator device is preferably not disposed in packaging and has a backing portion in facing the dilator alignment structure and the adhesive portion for adhering same to the tissue facing the user. The dilator alignment structure may have a substantially flat dilator receiving and retaining surface or same may be formed in a curving topography similar to the topography of the nose of a user. Preferably, the topography of the dilator alignment structure is customized for each user but using either a mold of the nose of a user. In this regard, a digital rendering of the nose may be created and used to form the topography of the alignment structure. Preferably said topography includes a shallow depression or groove for receiving and retaining the dilator device. The dilator alignment structure may be formed of resin, plastic, ceramic, paperboard, cardboard, rubber, latex, or other material and may be colored or clear or any combination thereof.

An alternative form of the embodiment just described comprises a disposable dilator alignment structure incorporating at least one dilator device disposed in preparation for application by a user. Preferably, each such disposable dilator alignment structure is formed of a relatively thin sheet of material configured as a compact multi-unit stack of such structures. Accordingly, each one of said stack of several such structures may be linked to a next unit so that when a first, or adjacent, unit is removed from the stack, a release liner for the adhesive layer is removed from the dilator device. The release liner may be retained by or on a next successive unit or may be merely temporarily retained so that the user may simply manually align the dilator alignment structure and create contact between the adhesive portion of the dilator device and the tissue to be dilated. The dilator alignment structure may be formed of sheet material and vacuum formed, molded, pressed and the like into a shape that may be stacked. A disposable form of this embodiment is preferably made of recyclable materials and may be colored, clear any combination and may employ any of a variety of alignment features to aid the user in correctly locating the dilator device in relation to nasal tissue to be dilated (as described below).

Custom Alignment Structures.

A user may create a custom dilator alignment structure according to this embodiment of the invention for use as described hereinabove. The process for creating such a custom dilator alignment structure includes forming an impression of the nose of the user in a soft primary or intermediate material, processing said soft primary of intermediate material to make it rigid in the shape of the nose. The primary soft or intermediate material may comprise an open or closed cell foam material, a sheet of temperature sensitive form-retaining material (or aluminum foil and the like), a gel material disposed in an open sided vessel, a plaster or casting material, or another type of material which temporarily retains the shape of an object impressed into said material (e.g., plurality of closely situated pin members slideably disposed in a frame). The primary soft or intermediate material is then processed to a more usable, rigid form applying heat, extracting heat, and the like so that the resulting structure closely conforms to the topography of the nose of the user.

Alignment Cues for Alignment Structure.

The alignment structure preferably includes at least one form of the following alignment cues, for use in accurately and correctly applying the dilator device to the nasal tissue to be dilated. The alignment features may be aligned with reference to the bridge of the nose, the tip of the nose, of a longitudinal axis of the face of the user. The type and configuration of a selected dilator alignment structure will at least partially dictate which of the alignment cues are effective (e.g., if the alignment structure is an open-ended, conical structure the bridge or tip of the nose will likely provide the best alignment cues). If the alignment structure comprises a substantially cylindrical shape, then the nostrils or tissue disposed laterally adjacent the nose may provide the best alignment. The alignment cues may be visual (e.g., a reflective surface, a line, a dot, a design or other indicia) or may be tactile (e.g., one or more ridges, apertures, detents, lips, textured areas and the like) or a combination of visual and tactile cues. Another embodiment of an alignment cue exploits an optical phenomenon observed when two spaced apart spots or other indicia disposed on a base material appear to optically merge as the base member is moved progressively closer to the nose of a subject. Due to the symmetry between the eyes of the subject, the spots or indicia appear to merge only when the midpoint of the base touches the user's nose. This embodiment comprises two spaced apart indicia on a base member wherein the base member is adapted to releasably retain a dilator device across the midpoint of the base member. In this form of the invention the base member may be adapted to dispense more than one dilator. For example, a single dilator may be adhered to or mechanically coupled to each side of the base member or the base member may have several dilator devices disposed within a compartment coupled to the base member. Such a compartment may provide a biasing force to each or every of the dilator devices so that when a dilator is dispensed therefrom, subsequent dilator devices are readily accessible to the subject. This form of the invention may be used with many diverse types of dilator devices. Of course, due to the different horizontal elevation of the eyes with respect to the appropriate effective mounting location of a given dilator, the spots or indicia on the base member may preferably share a similar relation to the dilator disposed thereon. In lieu of or in addition to spots or indicia, other structure may provide equivalent functionality, such as apertures, ports or a source of illumination (e.g., light emitting diodes). In use, removal of any release liner covering on the adhesive material typically used to couple the dilator to the subject should occur so that the dilator at least temporarily and accurately couples to the subject upon first contact. The base member may be curved with a constant or changing radius, or may have a complex geometrical cross section. The base member may have elongate features upon which the spot or indicia are disposed when extend from the location where the dilator is disposed (e.g., may be more than one piece having several elevations relative to the subject's eyes and nose).

Triangle-Shape Dilator including Mounting Aid.

Another embodiment of the present invention is an aid to mounting a dilator device that is preferably fabricated and packaged with a single dilator device and which may be readily dispensed using the apparatus of the present invention. This embodiment preferably comprises an elongate release liner extending the majority of the length of a dilator and which is selectively adhered near the longitudinal center axis on the outer portion of a dilator device. Thus, when the two end portions of the release liner are separated from the dilator device they may be bent to form a triangle shape. The user simply grasps a portion of the triangle shape and presses the dilator device to the ridge of the nose. The accuracy of placement using the triangle shape appears to relate to the fact that nearly every person can consistently accurately touch the ridge of their own nose.

Loop-Shape Dilator including Mounting Aid.

A related embodiment of the foregoing embodiment uses a selectively adhered release liner designed to be rolled into a loop for ease of handling and accurately applying a dilator device. Either one or two such loops may be advantageously employed for a single- or two-handed mounting feature. In the event that two loops are formed and handled by a user each such loop is preferably disposed on opposing sides of the ridge of the user's nose.

On-Dilator Loop Configuration.

A further refinement of the loop embodiment just described involves the further element of an elongate, semi-resilient member coupled to the release liner wherein first end of said semi-resilient member is adhered to a dilator device and the second end of the semi-resilient member has a touch sensitive adhesive bonded thereon. Thus, when a user bends the semi-resilient member into a loop and adheres the second end to the dilator, an additional lifting force is imparted to the dilator and, thus, to the adjacent region of tissue influenced by the dilator device. This embodiment creates the lifting force by generating tension, or a restoring force, at each end of the semi-resilient member when it is bent. The term "semi-resilient" is used herein in reference to the relative strength of magnitude of a resilient member presently manufactured and commercially distributed by CNS, Inc. of Minnesota, U.S.A. under the Breathe Rite® nasal dilator brand of CNS, Inc.

A further embodiment of the semi-resilient member just described includes adjustability of the magnitude of the lifting force imparted by the looped, semi-resilient member. In this embodiment, a first adhesive composition disposed on the second end of the semi-resilient member fully adheres to the back of the dilator device at one of several locations having a second adhesive composition. Thus, the user selects where to adhere the second end of the semi-resilient member prior to applying the dilator device to a region of tissue and thereby adjusts the lifting force. Each of the several locations are preferably marked with indicia indicating which locations will generate a greater force than other of said locations as a guide to the user.

Curl-Type Dilator for Single Area Dilation.

The embodiment just described in the above paragraph readily lends itself to application to a single portion of tissue; for example, on one side of a user's nose. In this embodiment, an elongate single-side dilator device comprises a semi-resilient member adhered at a first end and on the back side of an elongate base member. The base member has a layer of adhesive preferably covering the entire front side of the base member so that the base member may be advantageously positioned adjacent a region of tissue to be dilated. The second end of the semi-resilient member has a layer of touch sensitive adhesive disposed thereon so that a user can curl the semi-resilient member away from the base member and adhere the second end thereof to a region of tissue to be dilated. A slight modification of this particular embodiment includes a suction-type cup or enlarged foot member with a layer of adhesive to promote effective contact with the region of tissue and to distribute the lifting force over a larger area of tissue. Of course, the suction-type cup and enlarged foot member may be scaled to different sizes or contact areas as dictated by the use of the dilator device.

Sheet-Type Curl and Loop-Type Dilators.

Along the lines of the curl- or loop-type dilator devices just described is a family of compact dilator devices which are intend to be curled or looped by the user to develop a lifting force to a region of tissue. Each member of this family of dilator devices is intended to be manufactured and shipped as a thin sheet of material incorporating semi-resilient members which may be curled or looped by a user and adhered to a region of tissue. These dilator devices maybe adapted to provide an off-axis dilating, or lifting, force. That is, when looped or curled by a user, the body of the resilient member does not need to be in a common axis with the first end and the second end of the semi-resilient member. In a preferred form of this embodiment, the dilator device is a nearly unitary structure having an arbitrary shape, such as a circle, square or rectangle or other shape conducive to manufacturing, compact packaging and ease of use and which provides dual curl- or loop-type dilators which each provide lifting force to different regions of tissue. For example, a rectangular shape according to this embodiment, has adhesive only at a central location of the rectangular dilator device. A pair of serpentine (or at least C-shaped) semi-resilient dilator members emanate from the central adhesive location at a common end and end at respective second ends adjacent and just slightly spaced apart. The second ends share a common patch of touch sensitive adhesive with the central location thereby simplifying mass fabrication of the dilator devices. First, the central location base region is adhered to a region of tissue. Next, one of the pair of dilator members is remove from the release liner and curled back and away from its original location and adhered to adjacent tissue thus providing lifting force to said adjacent tissue. This particular embodiment may be configured into visually pleasing shapes when installed for use on tissue of a user. For example, a heart shape may be readily formed by slightly modifying the arbitrary shape of the dilator, or a butterfly shape may be constructed according to this form of the invention. The cross section of the semi-resilient member may vary to promote a smooth shape to the curl or loop and to increase the lifting force of the dilator device.

Note that in all these so-called curl- or loop-type embodiments the semi-resilient member may be fully or partially curled. These embodiments may be adhered to a region of tissue on either side of the curled or looped portion of the dilator device, since it is believed that both configurations generate sufficient lifting force to successfully dilate issue overlying nasal passageways in human users. Furthermore, some of the curl- and loop-type dilator devices provide the user with a form of handle to manipulate the dilator and thereby promote accurate alignment of the dilator device.

Miscellaneous Considerations.

In each embodiment of the present invention, more than one type, size or "strength" (i.e., lifting force) dilator device may be made available to a user. In addition, the dilator dispenser devices of the present invention may be configured to deliver a variety of adhesive-backed dilator devices (e.g., from a relatively weak adhesive to a relatively strong adhesive) which are designed for a variety of skin conditions.

Desk calendar:

While not depicted herein, but in this embodiment of the invention, a wall-, desk- or other surface-mounted "one a day" calendar which incorporates not only the date and other copy, graphic or icon (e.g., a cartoon) but also a dilator device. Such a calendar need not have a dilator device affixed for every day and each individual dilator device may be the same or different from other of said dilator devices (e.g., different scents having a seasonal theme or other motif and the like). Subscriptions could be sold so that the subject would receive one or two months of the calendar/dilator combination (complete and integrated or in the form of refills for the base calendar dispenser) at the appropriate time or upon request.

The invention claimed is:

1. A dispenser for nasal dilator devices, said dispenser comprising:
 a package;
 a connected plurality of nasal dilator devices contained within the package; and an aperture in the package through which each of the plurality of nasal dilator devices pass prior to being separated from the other nasal dilator devices;

wherein the package includes a cutout portion sized in relation to nasal surfaces of an intended user, and wherein a nasal dilator device is positioned within the cutout portion prior to usage of the nasal dilator device.

2. The dispenser of claim 1 wherein the connected plurality of nasal dilator devices is provided in roll form within the package.

3. The dispenser of claim 2 wherein the plurality of nasal dilator devices is provided upon a first roll rotatably supported within the package.

4. The dispenser of claim 1 further comprising a flexible tape for connecting the plurality of nasal dilator devices.

5. The dispenser of claim 4 wherein each of the plurality of dilator devices is adhesively secured to a surface of the tape.

6. The dispenser of claim 3 further comprising a second roll.

7. The dispenser of claim 6 further comprising a flexible tape connected between the first roll and the second roll, said tape having the plurality of nasal dilator devices attached thereto.

8. The dispenser of claim 7 wherein the second roll is adapted for rotation by a user through one or more of: a handle or a finger wheel.

9. The dispenser of claim 7 wherein rotation of the second roll advances dilator devices from the first roll toward the second roll.

10. A dispenser for providing nasal dilator devices to a user, said dispenser comprising:

a package adapted to be grasped by the user;

a connected plurality of nasal dilator devices contained within the package; and a passage through the package, wherein each of the plurality of nasal dilator devices passes through the passage and is separated from the other nasal dilator devices;

wherein the package includes a cutout portion sized in relation to nasal surfaces of the user, and wherein a nasal dilator device is positioned within the cutout portion prior to usage of the nasal dilator device.

11. The dispenser of claim 10 wherein the connected plurality of nasal dilator devices is provided in roll form within the package.

12. The dispenser of claim 11 wherein the plurality of nasal dilator devices is provided upon a first roll rotatably supported within the package.

13. The dispenser of claim 10 further comprising a flexible tape for connecting the plurality of nasal dilator devices.

14. The dispenser of claim 13 wherein each of the plurality of nasal dilator devices is adhesively secured to a surface of the tape.

15. The dispenser of claim 12 further comprising a second roll.

16. The dispenser of claim 15 further comprising a flexible tape connected between the first roll and the second roll, said tape having the plurality of nasal dilator devices attached thereto.

17. The dispenser of claim 15 wherein the second roll is adapted for rotation by a user through one or more of: a handle or a finger wheel.

18. The dispenser of claim 17 wherein rotation of the second roll advances dilator devices from the first roll toward the second roll.

19. A method of dispensing and applying a nasal dilator to a nasal surface, said method comprising the steps of:

providing a package having a cutout portion and a connected plurality of nasal dilator devices contained therewithin;

advancing one of the connected plurality of nasal dilator devices into the cutout portion of the package;

grasping the package and directing the cutout portion of the package toward nasal surfaces of a user;

contacting the nasal surfaces with the one nasal dilator device; and removing the package away from the nasal surfaces of the user.

20. The method of claim 19 further comprising the steps of:

providing the connected plurality of nasal dilator devices upon a first roll contained within the package; and rotating the first roll to advance the nasal dilator devices out of the package.

21. The method of claim 20 further comprising the steps of:

providing the connected plurality of nasal dilator devices upon a tape, said tape being connected between the first roll and a second roll.

22. The method of claim 21 further comprising the steps of:

manually rotating the second roll to advance nasal dilator devices out of the package.

23. A dispenser for providing nasal dilator devices to a user, said dispenser comprising:

a package defining an interior region;

a plurality of releasably connected nasal dilator devices contained within the interior region of the package; and a passage through the package, wherein the plurality of nasal dilator devices pass in serial fashion through the passage;

wherein the package includes a cutout portion sized in relation to nasal surfaces of the user, and wherein a nasal dilator device is positioned within the cutout portion prior to usage of the nasal dilator device.

* * * * *